(12) United States Patent
Friedman

(10) Patent No.: US 11,260,075 B1
(45) Date of Patent: Mar. 1, 2022

(54) NON-THERMAL ATMOSPHERIC PLASMA TO TREAT HAIR LOSS

(71) Applicant: Peter Friedman, New City, NY (US)

(72) Inventor: Peter Friedman, New City, NY (US)

( * ) Notice: Subject to any disclaimer, the term of this patent is extended or adjusted under 35 U.S.C. 154(b) by 0 days.

(21) Appl. No.: 16/826,172

(22) Filed: Mar. 21, 2020

Related U.S. Application Data

(60) Provisional application No. 62/822,907, filed on Mar. 24, 2019.

(51) Int. Cl.
| | |
|---|---|
| *A61K 33/40* | (2006.01) |
| *A61K 9/00* | (2006.01) |
| *A61K 9/06* | (2006.01) |
| *A61K 9/08* | (2006.01) |
| *A61K 47/26* | (2006.01) |
| *A61K 47/38* | (2006.01) |
| *A61K 47/44* | (2017.01) |
| *A61K 45/06* | (2006.01) |

(52) U.S. Cl.
CPC ............ *A61K 33/40* (2013.01); *A61K 9/0014* (2013.01); *A61K 9/0019* (2013.01); *A61K 9/06* (2013.01); *A61K 9/08* (2013.01); *A61K 45/06* (2013.01); *A61K 47/26* (2013.01); *A61K 47/38* (2013.01); *A61K 47/44* (2013.01)

(58) Field of Classification Search
CPC .................................................. A61K 9/0019
See application file for complete search history.

(56) References Cited

U.S. PATENT DOCUMENTS

| | | |
|---|---|---|
| 9,226,790 B2 | 1/2016 | Zemel et al. |
| 2013/0041443 A1 | 2/2013 | Weissberg et al. |
| 2014/0079686 A1* | 3/2014 | Barman ................... A61K 8/69 424/94.67 |
| 2015/0111973 A1* | 4/2015 | Bauman ............... A61K 31/655 514/740 |

FOREIGN PATENT DOCUMENTS

| | | | |
|---|---|---|---|
| WO | WO-2012106735 A2 * | 8/2012 | ........... A61N 1/0472 |
| WO | PCT/US2015/049723 A1 | 3/2016 | |
| WO | PCT/US2017/044791 A1 | 2/2018 | |

OTHER PUBLICATIONS

D. Yan et al. Controlling plasma stimulated media in cancer treatment application. Appl. phys. lett. 2014. 105, 22410-1 to 22410-4. (Year: 2014).*
Google patent search_Feb. 26, 2021 (Year: 2021).*
Google search_Feb. 25, 2021 (Year: 2021).*
Bernhardt, Thoralf & Semmler, Marie & Schäfer, Mirijam & Bekeschus, Sander & Emmert, Steffen & Boeckmann, Lars. (2019). Plasma Medicine: Applications of Cold Atmospheric Pressure Plasma in Dermatology. Oxidative Medicine and Cellular Longevity. Jan. 10, 2019. 10.1155/2019/3873928.
Barolet D, Benohanian A. Current trends in needle-free jet injection: an update. Clin Cosmet Investig Dermatol. May 1, 2018;11:231-238. doi: 10.2147/CCID.S162724. PMID: 29750049; PMCID: PMC5936486.
Fridman, G., Friedman, G., Gutsol, A., Shekhter, A.B., Vasilets, V.N. and Fridman, A. (2008), Applied Plasma Medicine. Plasma Processes Polym., 5: 503-533. https://doi.org/10.1002/ppap.200700154.
Babossalam, S., Abdollahimajd, F., Aghighi, M. et al. The effect of nitrogen plasma on the skin and hair follicles: a possible promising future for the treatment of alopecia. Arch Dermatol Res 312, 361-371 (2020). https://doi.org/10.1007/s00403-019-02020-w.

\* cited by examiner

*Primary Examiner* — Michael P Cohen
(74) *Attorney, Agent, or Firm* — Elman Technology Law, P.C.; Gerry J. Elman; M. P. Moon

(57) ABSTRACT

Non-thermal Atmospheric Plasma (NAP) from a plasma source is mixed with a liquid medium and the resulting compound is applied to the scalp to treat hair loss. The NAP-medium compound may be applied to the surface of the scalp, or produced in situ, or injected into the scalp.

5 Claims, 18 Drawing Sheets

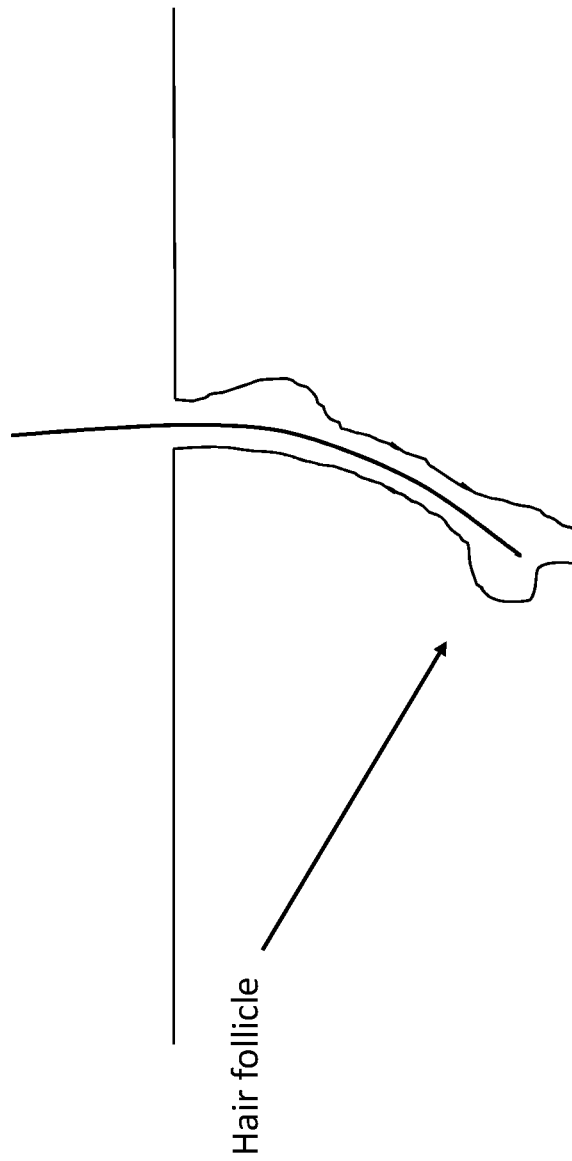

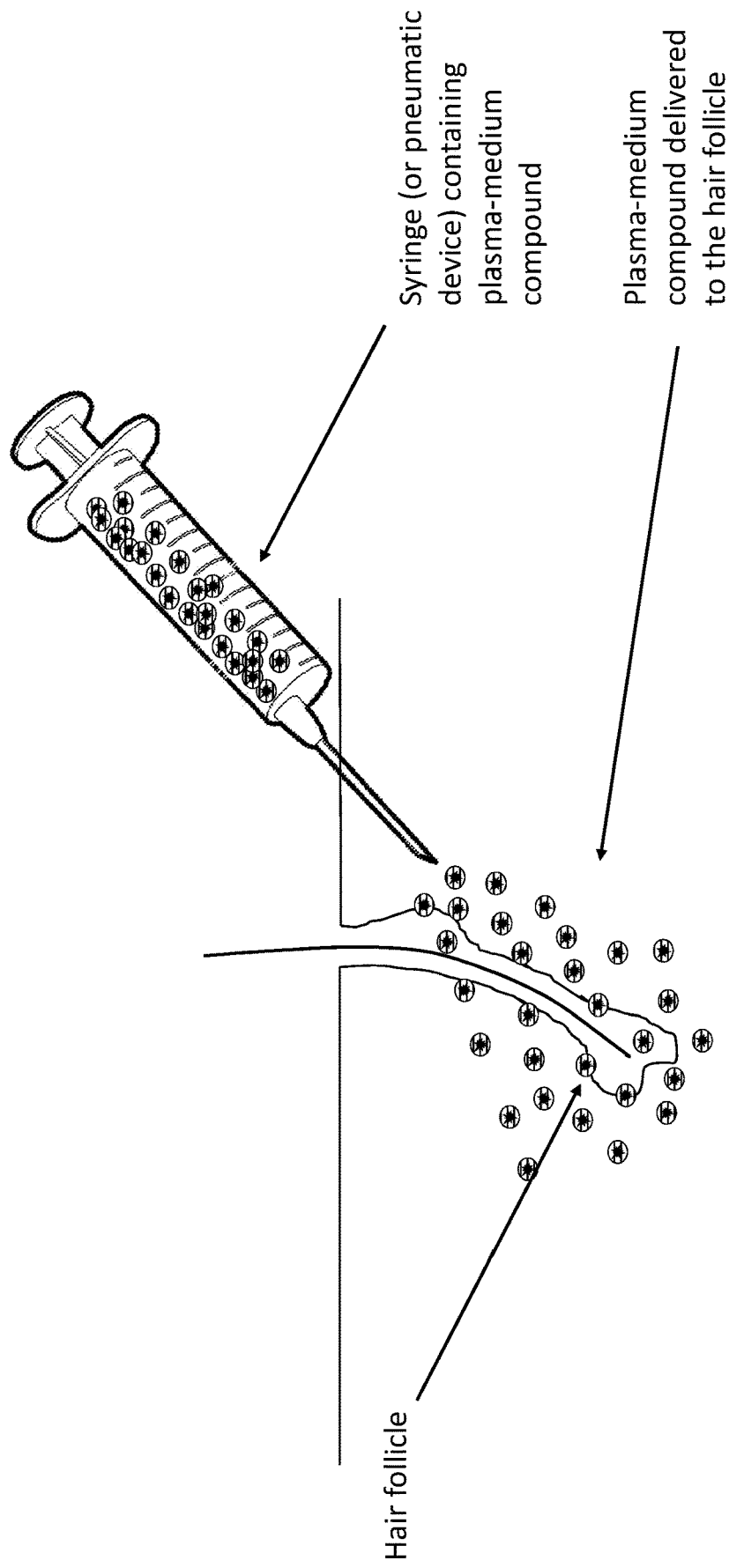

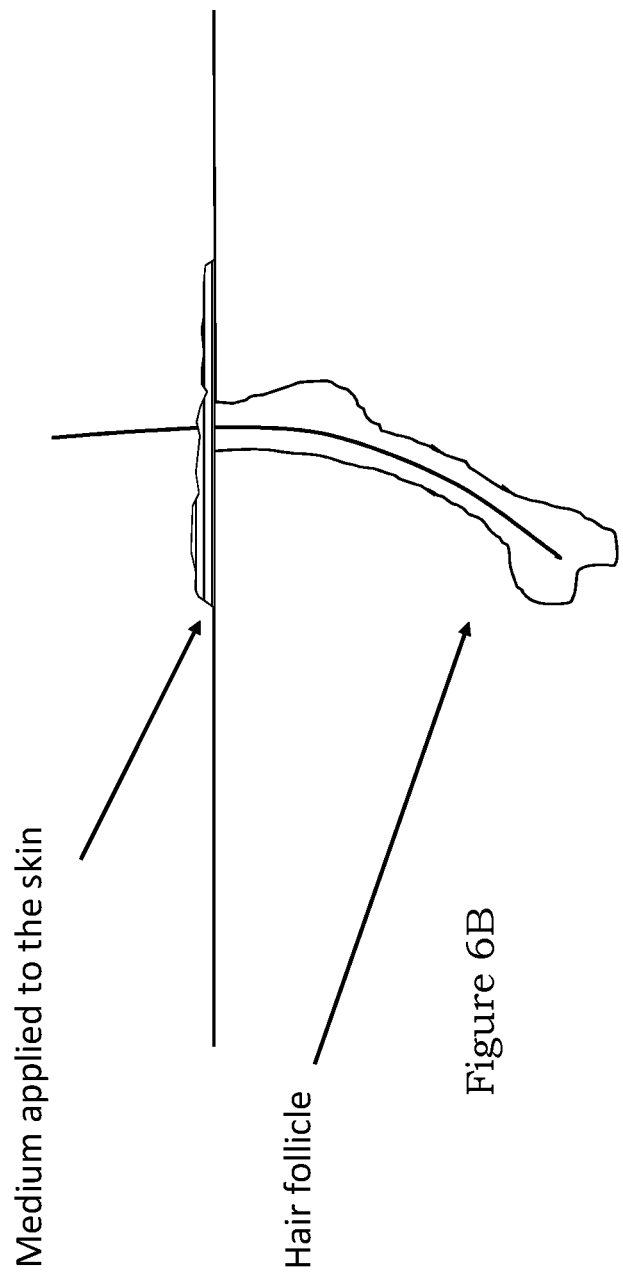

NON-THERMAL ATMOSPHERIC PLASMA TO TREAT HAIR LOSS

CROSS-REFERENCE TO RELATED APPLICATIONS

This non-provisional patent application claims the benefit of priority to U.S. Provisional Application No. 62/822,907 filed Mar. 24, 2019. The entire disclosure of the aforementioned application is incorporated herein by reference.

TECHNICAL FIELD

The present invention relates to substances useful for inducing hair growth and treating hair loss, and methods for making and using the substances to induce hair growth and treat hair loss.

BACKGROUND

In medicine, the term "plasma" typically refers to blood plasma. However, in physics, there is an alternative meaning associated with the term "plasma." In that context, it refers to a fourth state of matter (in addition to the classical three states: solid, liquid, and gas). Such a physical plasma can be generated by adding energy (heat or electromagnetic fields) to a neutral gas until the ionized gaseous substance becomes increasingly electrically conductive. Plasmas emit electromagnetic radiation, particularly UV radiation and visible light, and contain excited gas molecules, positively and negatively charged ions, free electrons, neutral reactive oxygen/nitrogen species (ROS/RNS), free radicals, and molecule fragments.
Man-made plasmas are classified as being thermal or non-thermal, based on the temperature generated in the system.

The temperature in the plasma system is determined by the average energies of the plasma particles both neutral and charged, i.e., electrons, neutrals, ions, and their relevant degrees of freedom. The degree of ionization in the plasma can vary from fully ionized gases (100%) to partially ionized gases. Thermal plasmas are often referred to as "hot" plasmas or equilibrium plasmas. If all particles (electrons, ions) are in energy equilibrium, meaning that they have the same very high temperature, hot plasma is obtained. Examples of hot plasma include the corona of the sun, the plasma in a fusion reactor, or a discharge arc such as in welding or arc lamps. In modern medicine, hot plasmas have been used for sterilization of medical devices and implants.

More pertinent to the present invention are non-thermal plasmas, which are produced near room temperatures. They are also known as "cold" plasmas or nonequilibrium plasmas. Compared to "regular" gas where entire molecules or atoms move freely, plasma is in a higher energy state where atoms lose their electrons—become ionized—and the resulting electrons and ions move freely and independently from each other. Non-thermal plasmas have the ions and neutrals at a much lower temperature, whereas the electrons are much "hotter." Due to the low density of the gas, collisions with the other species are relatively rare, and thermal equilibrium is not achieved. Cold plasmas can be generated at various pressures, ranging from vacuum pressure to atmospheric pressure.

Cold plasma, preferably at atmospheric pressure, is employed in the practice of the present invention. In this patent, such plasmas are called "Non-thermal Atmospheric Plasma" (NAP). Alternative terms for them are "Cold Atmospheric-Pressure Plasma" (CAP or CAPP). The main active components of such plasmas are reactive oxygen and nitrogen species, but they may also contain other reactive species and charged particles.

SUMMARY

The present invention provides a method of delivering components of physical plasma, the fourth state of matter, to the skin and hair follicles to induce growth of hair to treat any form of hair loss. Non-thermal Atmospheric Plasma (NAP) is combined with appropriate media to allow its delivery to targets, especially where direct contact with plasma would be impossible or ineffective. The present invention also relates to methods of making novel NAP-medium compounds and to such compounds.

An aspect of the present invention is a NAP-medium compound for providing Non-thermal Atmospheric Plasma (NAP) treatment to the skin of a patient, comprising a medium selected from the group consisting of water, other aqueous media, and water-soluble media, and non-thermal atmospheric plasma (NAP) generated from a plasma source.

In some embodiments of the invention, the medium is formulated as a lipophilic cream, a hydrophilic cream, an ointment, a lotion, or a gel vehicle.

The present invention also provides a method of making a NAP-medium compound for ameliorating hair loss by starting with a medium selected from the group consisting of aqueous, alcohol, and aqueous alcohol solutions comprising individually or in combination water, saline, phosphate buffered saline, Ringer's lactate solution, culture medium, PRP, and one or more alcohols selected from the group consisting of methanol, ethanol, isopropanol, propylene glycol, glycerol, and lanolin alcohol; and then treating the medium with NAP that is generated from a plasma source.

The present invention also contemplates novel NAP-medium compounds prepared by the aforesaid method and its specific variants.

The invention contemplates the method of ameliorating hair loss by applying a medium selected from the group consisting of water, other aqueous media, and water-soluble media, and non-thermal atmospheric plasma (NAP) generated from a plasma source. to an affected area at least once a day for at least a month.

A variant of the aforesaid method comprises the following steps:
  generating a suitable NAP-medium compound from a suitable pharmaceutically-acceptable medium;
  introducing the NAP-medium compound into a syringe-type device;
  injecting the NAP-medium compound into the scalp subcutaneously;
  allowing the NAP-medium compound to permeate the hair follicle area to induce growth;
  wherein the pharmaceutically acceptable medium is selected from the group of ethanol, glycerin, isopropyl alcohol, methanol, propylene glycol, water, saline, phosphate buffered saline, culture medium, Ringer's lactate solution, PRP blood plasma, and mixtures thereof.

Another such variant comprises the following steps:
  applying a pharmaceutically-acceptable medium to the affected area of the scalp,
  treating the medium present on the scalp with NAP from a plasma source; and
  allowing the resulting in situ-generated NAP-medium compound to remain on the affected area of the scalp, whereby it penetrates the scalp sufficiently to provide the hair-growth inducing effect of NAP;

wherein, the medium consists essentially of one or more of water, saline, phosphate buffered saline, culture media, Ringer's lactate solution, platelet rich blood plasma (PRP), methanol, ethanol, isopropanol, propylene glycol, glycerol, lanolin alcohols and mixtures thereof.

Additional features and aspects of the present invention are set forth in the Detailed Description presented below.

BRIEF DESCRIPTION OF THE DRAWINGS

FIG. 5A is diagrammatic magnified view of a cross-section of a subject's scalp, showing a hair follicle before being treated via a second method of the present invention.

FIG. 5E is a diagrammatic magnified view of the cross-section of FIG. 5D taken at a time after that of FIG. 5D, showing NAP-medium compound being injected intralesionally and thereby being delivered to the hair follicle.

FIG. 6B is a diagrammatic magnified view of the cross-section of FIG. 6A, wherein an untreated medium has been applied to the skin of the subject's scalp.

DETAILED DESCRIPTION

Figure 1:
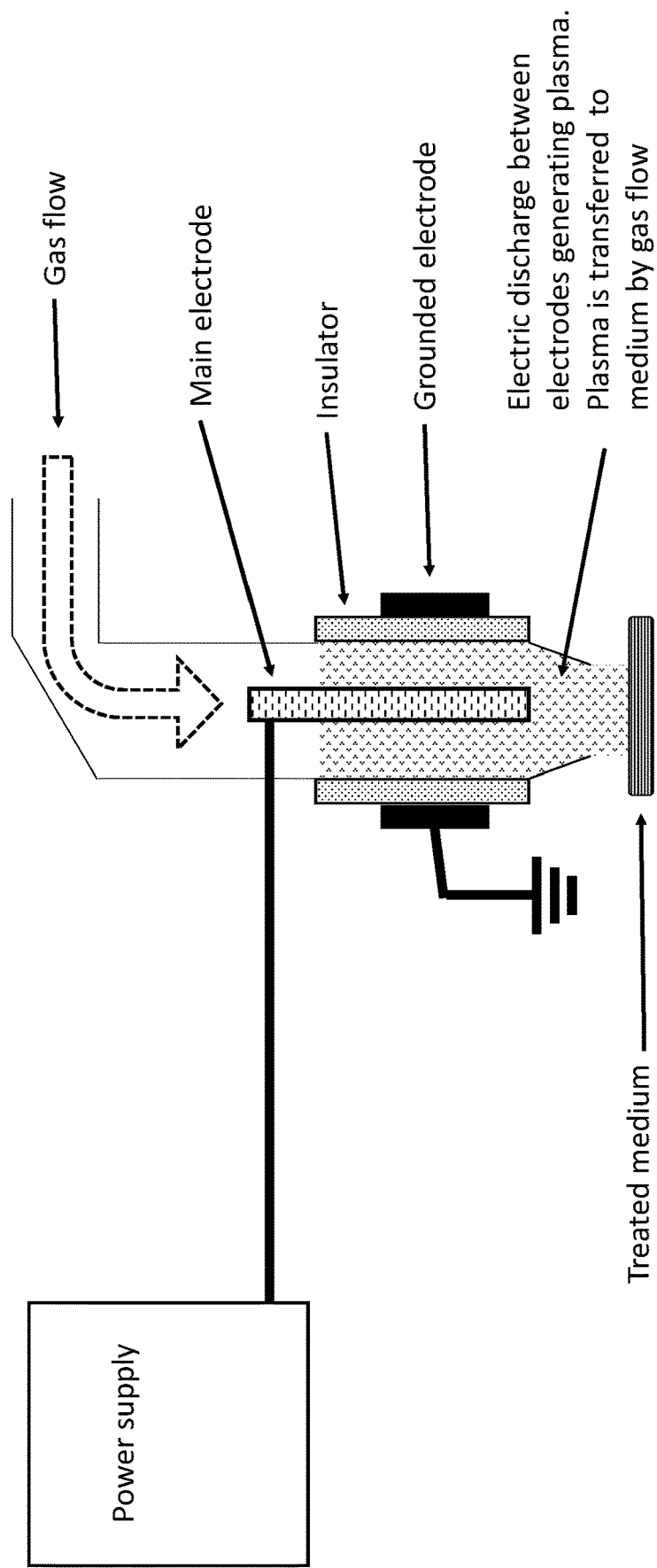
FIG. 1 is a schematic diagram of a plasma jet suitable for performing the present invention.
Figure 2:
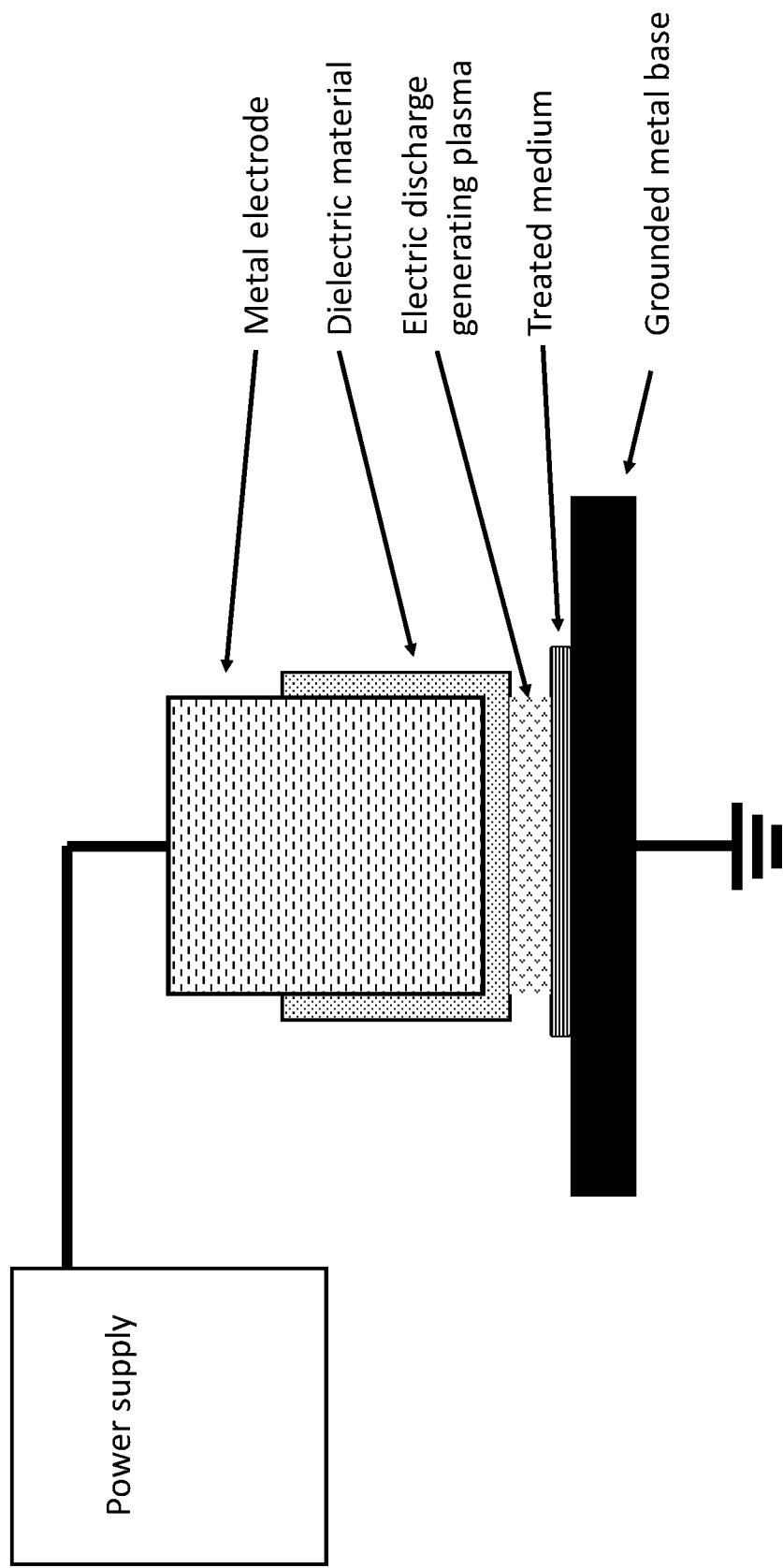
FIG. 2 is schematic diagram of a dielectric barrier discharge (DBD) plasma device suitable for performing the present invention.
Figure 3:
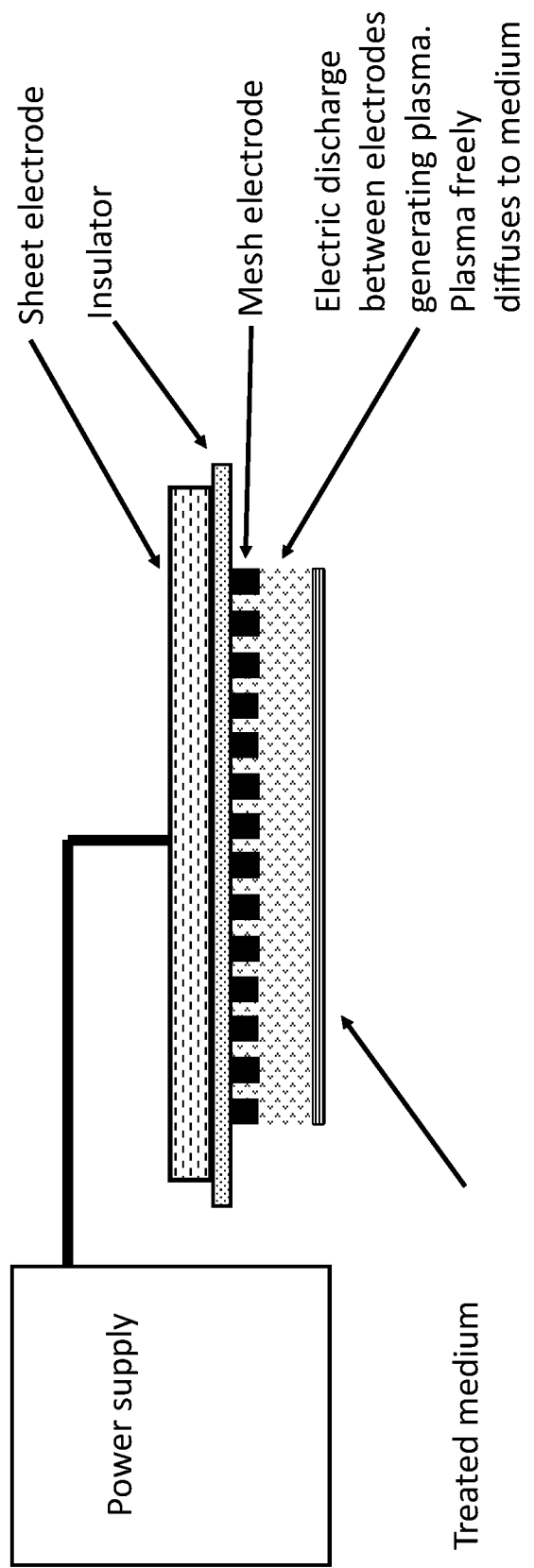
FIG. 3 is schematic diagram of a surface micro-discharge (SMD) plasma device suitable for performing the present invention.
Figure 4A:
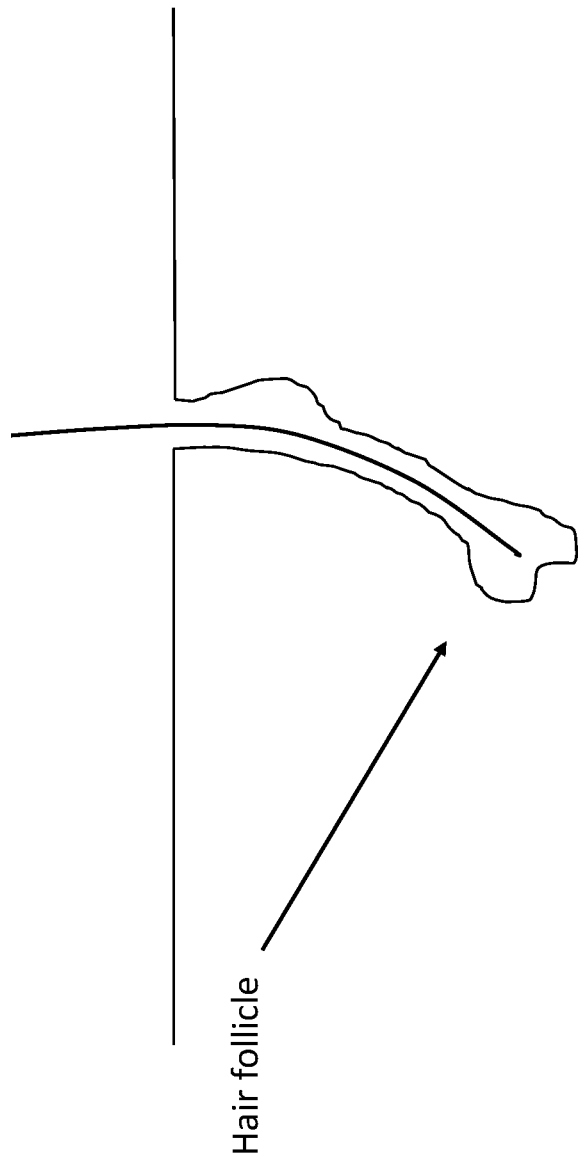
FIG. 4A is a diagrammatic magnified view of a cross-section of a subject's scalp, showing a hair follicle before being treated via a first method of the present invention.
Figure 4B:
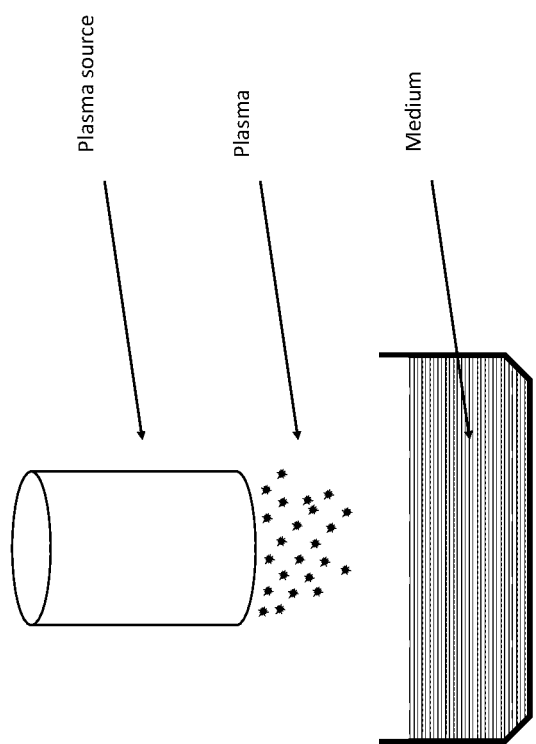
FIG. 4B is a diagrammatic elevation view of a plasma source generating plasma above a medium with the medium in a container shown in cross-section.
Figure 4C:
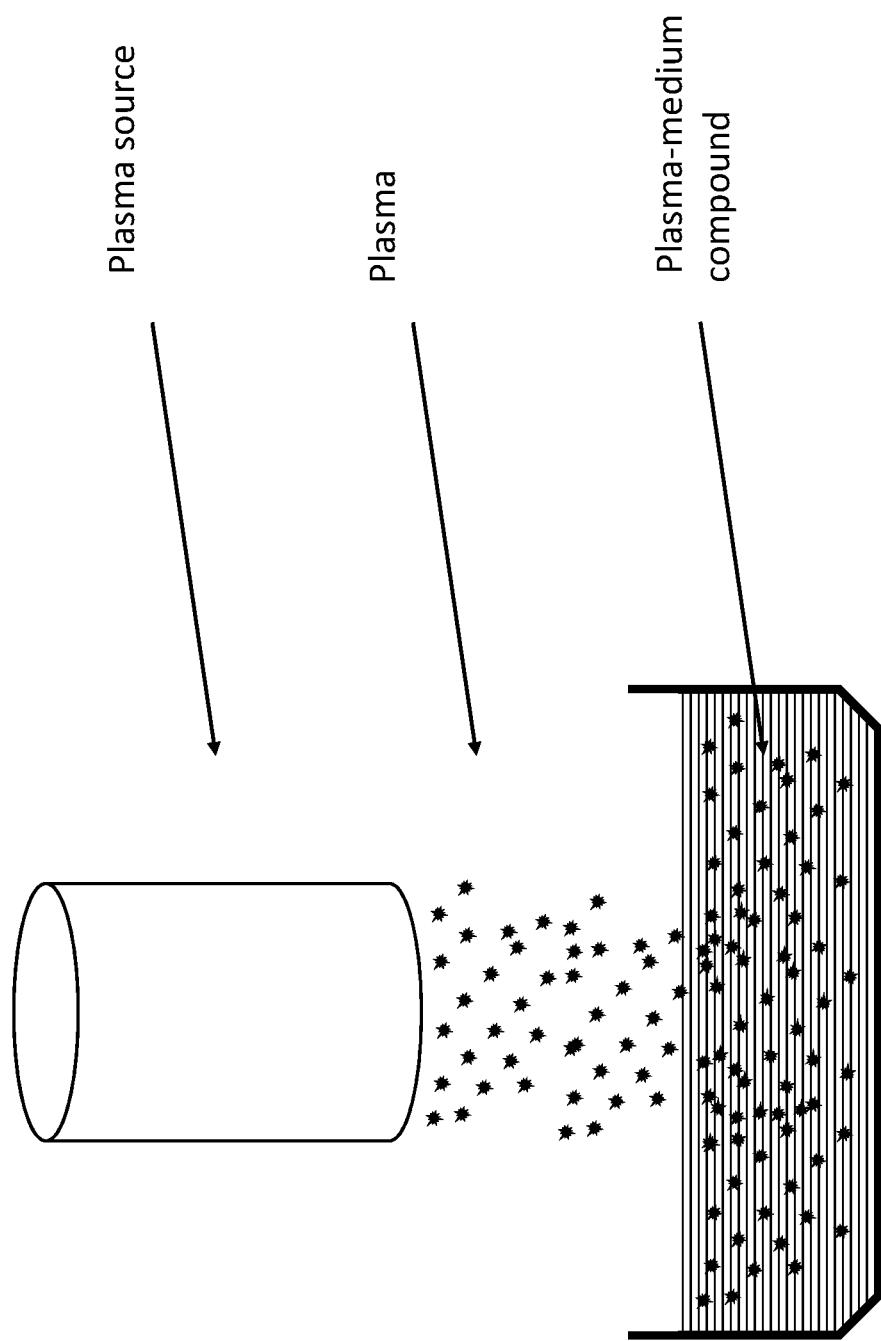
FIG. 4C is a diagrammatic elevation view of the setup of FIG. 4B taken at a time after that of FIG. 4B, wherein much of the generated plasma has been incorporated into the plasma, forming an NAP-medium compound of the present invention.
Figure 4D:
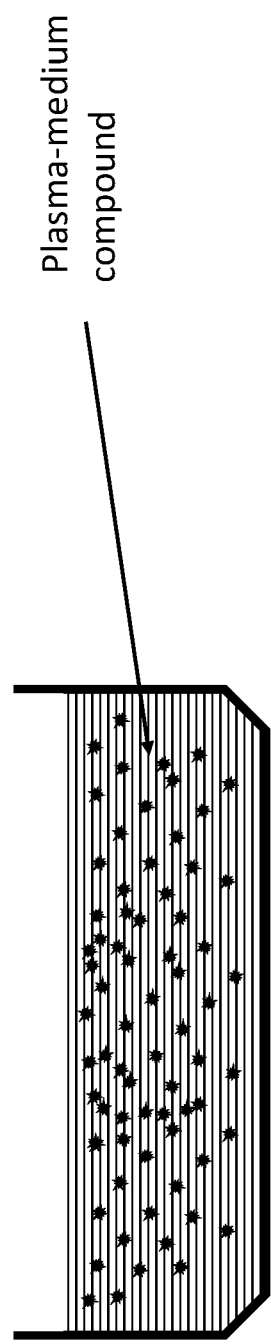
FIG. 4D is a diagrammatic elevation view of the container of FIG. 4C taken at a time after that of FIG. 4C, showing a plasma-medium compound of the present invention in a container.
Figure 4E:
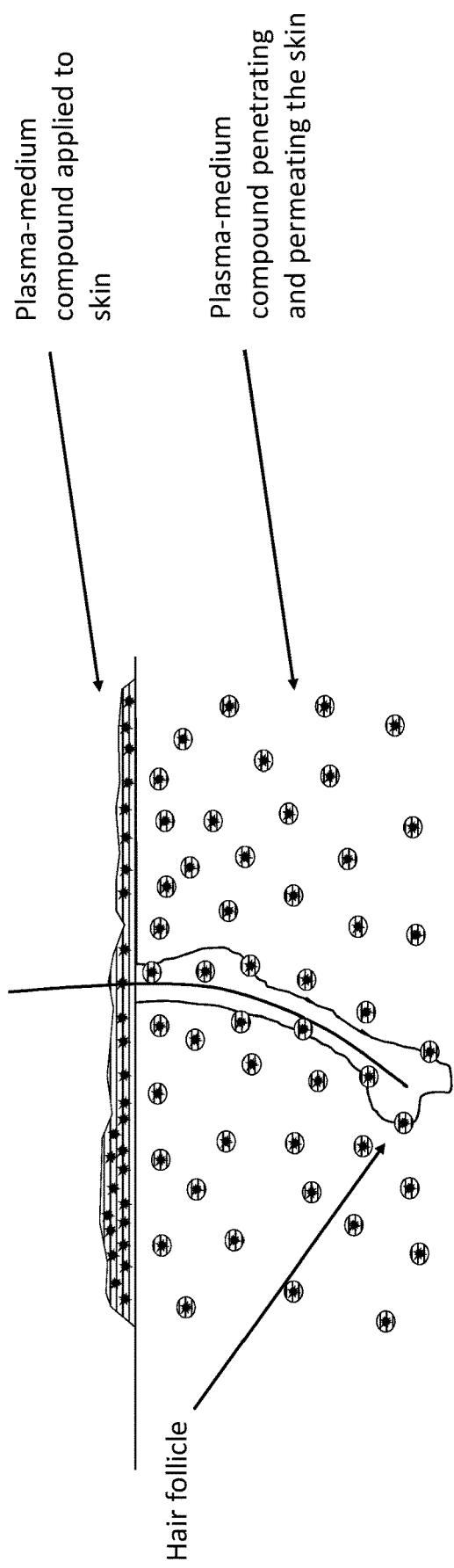
FIG. 4E is a diagrammatic magnified view of the cross-section of a subject's scalp wherein the plasma-medium compound of FIG. 4D has been applied to the skin and is shown penetrating and permeating the subject's scalp.

If Non-thermal Atmospheric Plasma ("NAP") is placed directly in contact with human skin, it would not be expected to penetrate deeply. To deliver the effect of NAP to the level of the hair follicle bulge region and the dermal papilla, the present invention employs a NAP-medium compound, which is applied directly to the scalp or injected beneath the dermal layer. The NAP-medium compound is comprised of a medium, and NAP and is prepared by treating the medium with NAP from a plasma source. Alternatively, a medium may be applied to the scalp and the medium is then treated with NAP to generate the NAP-medium compound in situ and deliver the effect.

The medium is a liquid which can optionally be formulated as a lipophilic cream, a hydrophilic cream, an ointment, a lotion, a gel vehicle, or mixtures thereof. The medium must be compatible with topical application to the skin surface and/or subcutaneous applications. The medium is desirably a fluid that is able to penetrate and permeate deep enough in the skin and pilosebaceous unit to reach the target follicle structures. The medium must also be compatible with NAP and capable of being treated with NAP without destroying its aforesaid properties.

For topical applications, one may select media for this purpose from among lipophilic substances and hydrophilic substances that are useful as vehicles or media for drugs to reach hair follicles. Suitable media for the effective delivery of NAP include water, other aqueous media, and water-soluble media. Examples of aqueous media contemplated for the invention include, water, saline, phosphate buffered saline, culture medium, Ringer's lactate solution, platelet rich blood plasma (PRP), and the like. Suitable water soluble media include alcohols, particularly monohydroxy-alcohols, polyhydroxy-alcohol, or mixtures of monohydroxy- and/or polyhydroxy-alcohols. Examples of suitable alcohol media of the invention include ethanol, methanol, isopropanol, propylene glycol, glycerol, lanolin alcohols and the like.

"Culture medium" is a liquid or gel designed to support the growth of microorganisms. There are different types of media suitable for growing different types of cells. Suitable culture media are liquid nutrient media, for example lysogeny broth, Preferred media for effective delivery of the NAP include aqueous alcohol solutions. The alcohol component is comprised of a monohydoxy-alcohol, a polyhydroxy-alcohol, or a mixture of monohydroxy- and/or polyhydroxy-alcohols. Typical monohydroxy-alcohols suitable for producing compositions of the invention include, methanol, ethanol, isopropanol and the like. Typical polyhydroxy-alcohols include, propylene glycol, glycerol, lanolin alcohols and the like.

The aqueous component may be water, saline, phosphate buffered saline, culture media, Ringer's lactate solution, PRP blood plasma, and the like.

A typical two-component medium will have an alcohol component in the range of 20-70% alcohol with the remainder being an aqueous component.

When mixtures of two alcohols are used as the alcohol component, the ratio of alcohols may be between 1/10 and 1/1 volume to volume. A typical three-component medium may be comprised of ethanol or isopropyl alcohol 10%-80%, propylene glycol 5-30%, and water or saline solution 10-80%.

To enhance the duration and effectiveness of contact of the NAP-medium compound, it may be further formulated as a lipophilic cream, a hydrophilic cream, an ointment, a lotion, a gel vehicle, or mixtures thereof. See, e.g. A. Oakley (Hamilton, NZ), Topical formulations. DermNet NZ https://dermnetnz.org/topics/topical-formulations/ Such formulations may be prepared either before or after treating a suitable medium with NAP. Lipophilic creams and ointments have as the continuous phase (larger component) the lipophilic phase. They typically contain water-in-oil emulsifying agents such as lanolin, sorbitan esters and monoglycerides. Hydrophilic creams have as the continuous phase (larger component) the aqueous phase. Lotions are liquid formulations that are usually simple suspensions or solutions of medication in water, alcohol or other liquids. Gels are aqueous or alcoholic monophasic semisolid emulsions. They may be based on cellulose and formulated to liquefy upon contact with skin.

For injectable applications wherein the NAP-treated medium is introduced subcutaneously, the medium will be selected from among pharmaceutically-acceptable media. such as ethanol, glycerin, isopropyl alcohol, methanol, propylene glycol, water, and the like. It is preferred that aqueous media be selected for subcutaneous applications. Examples of aqueous media contemplated for the invention include water, saline, phosphate buffered saline, culture media, Ringer's lactate solution, PRP blood plasma, and the like.

In an embodiment of the invention wherein the NAP complements the effect of another active agent, the medium in this instance may be human blood plasma. Typically it is platelet-rich plasma (PRP) also known as autologous conditioned plasma. Injected into the scalp, PRP is sometimes currently used to treat hair loss.

PRP has enhanced platelet concentration and is generally produced from the patient's own blood. To generate PRP, blood is drawn from the patient and then spun in a centrifuge utilizing special tubes with separator gel to capture red blood cells. The portion of plasma supernatant with highest platelet concentration is removed and used for formulation of the medium to be treated with NAP.

The medium may further comprise additives routinely used in manufacturing topical medications. Such additives include lipids, emulsifiers, humectants, penetration enhancers, preservatives, bacteriostatic agents, stabilizers, and other additives.

Typical lipids include castor oil, cetyl alcohol, cocoa butter, isopropyl myristate, isopropyl palmitate, lanolin, liquid paraffin, stearic acid, stearyl alcohol, and white soft paraffin (petrolatum).

Typical emulsifiers include alkyl sulphates and sulphonates, glyceryl monostearate, lanolin and derivatives, phosphoric acid esters, polyethylene glycols, polyvalent metallic soaps, propylene glycol fatty acid esters, quaternary ammonium cationic compounds, sorbitan monolaurate, monopalmitate and mono-oleate, triethanolamine oleate.

Typical humectants include gelatin, glycerin, propylene glycol, pyrrolidone carboxylic acid, sorbitol, and urea.

Typical penetration enhancers include azone, dimethyl sulfoxide, propylene glycol, salicylic acid, and urea.

Typical preservatives and bacteriostatic agents include benzyl alcohol, butylated hydroxyanisole, butylated hydroxytoluene, chlorocresol, edetic acid/disodium edetate, hydroxybenzoates (parabens), propylene glycol, sodium metabisulphite, and sorbic acid/sorbates.

The medium must be suitable not just for penetration and permeation into the skin but must also be treatable with plasma (NAP) without breaking down. As the chemical composition of the medium affects its "treatability," some compositions require longer exposure to NAP than others.

Exposure to the plasma source is adjusted for every specific composition to reach the desired level of plasma treatment. NAP is introduced to the medium via a plasma source such as a plasma jet, a dielectric barrier discharge (DBD) plasma device, or a surface micro discharge plasma device. (See, e.g., Plasma Medicine: Applications of Cold Atmospheric Pressure Plasma in Dermatology, Hindawi, Oxidative Medicine and Cellular Longevity. Volume 2019, Article ID 3873928, 10 pages doi.org/10.1155/2019/3873928)

As schematically represented in FIG. 1, a plasma jet employs a flow of a carrier gas traveling along an electrode which is connected to a high-frequency power source. The plasma discharge developing around the electrode is carried by the gas to the surface of the liquid.

Suitable

As schematically represented in FIG. 2, a DBD plasma device has a conductive metal electrode covered with a dielectric layer (quartz) that is placed close to the surface of the treated medium. Suitable metals for the electrode include aluminum, copper, iron, platinum, or other conductive metal. The base under the medium, which may be a thin-walled plastic container, is grounded. A high frequency electric pulse generator is connected to the electrode, resulting in electric discharges between the electrode and the surface of the treated medium. NAP is generated that diffuses into the medium.

As schematically represented in FIG. 3, a surface micro-discharge device uses a powered plane or sheet electrode and a mesh electrode. A high frequency electric pulse generator is connected to a plane or sheet electrode, resulting in electric discharges between the electrodes. The generated NAP diffuses into the medium.

Examples of commercially available plasma devices useful as plasma sources suitable for implementing the present invention include products from the following companies, as marketed under the following trademarks: neoplas tools GmbH (Greifswald, Germany) kINPen® MED; relyon plasma GmbH (Regensburg, Germany) Piezobrush® PZ2 & Plasmabrush®PB3; terraplasma GmbH (Garching, Germany) Plasma Care®.

The exposure time depends on the characteristics of the particular plasma source, on the medium, and on the volume of the medium. All of these variables can be adjusted to reach the intended outcome, namely, clinical growth of hair. The medium can be exposed to the electric discharges for a time in the range of about 1 minute to an hour. For the jet plasma treatment, typically 6 minutes of treatment are appropriate for each cc of liquid medium. However, the inventor has experimentally determined that an effective NAP-treated medium may be produced by exposing 2 cc of liquid medium for 5 minutes. Alternatively, 15 cc of liquid medium could be exposed to jet plasma for 1 hour to achieve a suitable NAP-treated medium. For the DBD plasma treatment, one may, for example, expose 5 cc of liquid for 30 minutes. For use with a surface micro discharge plasma source, one may, for example, expose 2 cc of liquid medium for 10 minutes and achieve a suitable NAP-treated medium.

The amount of plasma in the medium generally cannot be directly measured with certainty. So the treated mixtures are desirably assayed for effective potency of NAP using surrogate markers. For example, hydrogen peroxide concentration measured using commercially available test strips (e.g. Macherey-Nagel® 91333, Quantofix® Peroxide 1000). Such assay methods may alternatively measure free nitrogen radical concentration, electric charge, or other elements of plasma to provide an indirect means of determining the relative concentration.

The typical concentration of hydrogen peroxide in a given NAP-medium compound is about 100 mg/liter to 1,000 mg/liter. This can be achieved by adjusting plasma exposure and medium volume to reach the target concentration. It can also be reached to treat a smaller amount of medium to achieve a high concentration of hydrogen peroxide and then dilute it with non-treated medium until the NAP-medium compound reaches the desired hydrogen peroxide concentration.

For example, a NAP-medium compound with a measurable peroxide concentration of 1,000 mg/liter would be diluted before use so that the measurable hydrogen peroxide in the NAP-medium compound is about 300 mg/liter. Such media generally maintain their potency for at least one week. The patients can be provided with NAP-medium compound to apply to the treated areas of the scalp once or twice a day, every day, to produce the intended benefit.

After the NAP-medium compound is applied to the scalp, it is not removed or rinsed off. Instead, it is allowed to absorb into the scalp. Treatment is to be continued for as long as treatment is needed and for maintenance of the desired effect.

A NAP-medium compound can be used for intralesional injections. For that, a suitable medium, such as normal saline, is used. The NAP-medium compound may further comprise ethanol or other pharmaceutically acceptable component, applied cautiously. Using the same method as described above but appropriately adjusted exposure times, plasma treatment is performed on the medium. The NAP-medium compound is then injected into the scalp (or other treated hair-bearing areas of the skin) using a hypodermic needle. This method relies on physically delivering the NAP-medium compound to the targeted hair follicle rather than allowing it to penetrate and permeate through the skin.

For example, the area to be treated is disinfected using alcohol wipes or other disinfectant. The NAP-medium compound is transferred to a syringe, which is then attached to a small-gage hypodermic needle. The needle is inserted into the skin horizontally or at a small diagonal angle, taking care that the tip of the needle reaches the estimated depth of the hair follicle. Then 0.1-0.5 cc NAP-medium compound is slowly injected into the skin, and then the needle is slowly withdrawn. Injection sessions are performed at selected intervals, e.g. from once a week to once a month.

The medium used for intralesional injections is selected from pharmaceutically-acceptable media used for injected medications, such as ethanol, glycerin, isopropyl alcohol, methanol, propylene glycol, water, and the like. It is preferred that aqueous media be selected for intralesional injections. Examples of such aqueous media include water, saline, phosphate buffered saline, culture medium, Ringer's lactate solution, PRP blood plasma, and the like.

Figure 5B:
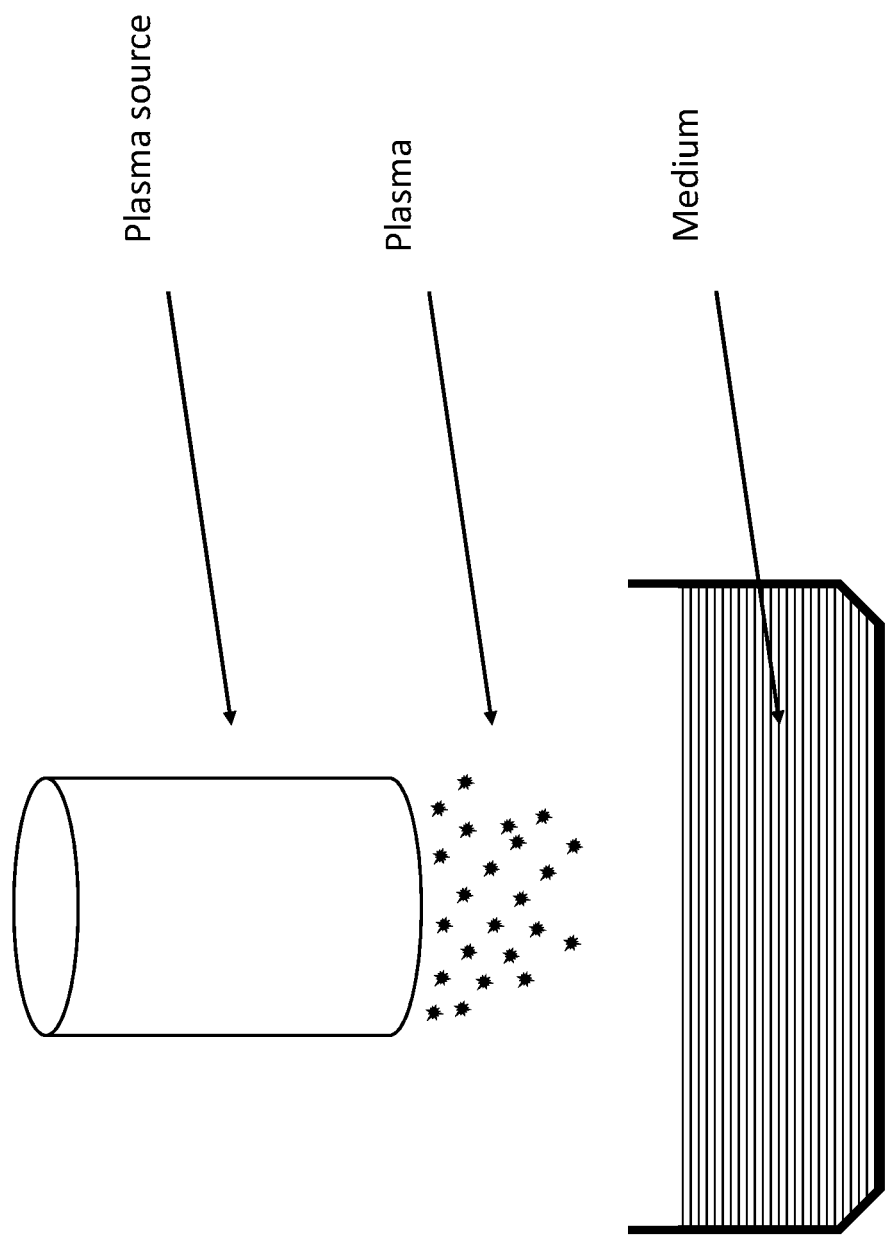
FIG. 5B is a diagrammatic elevation view of a plasma source generating plasma above a medium with the medium in a container shown in cross-section.
Figure 5C:
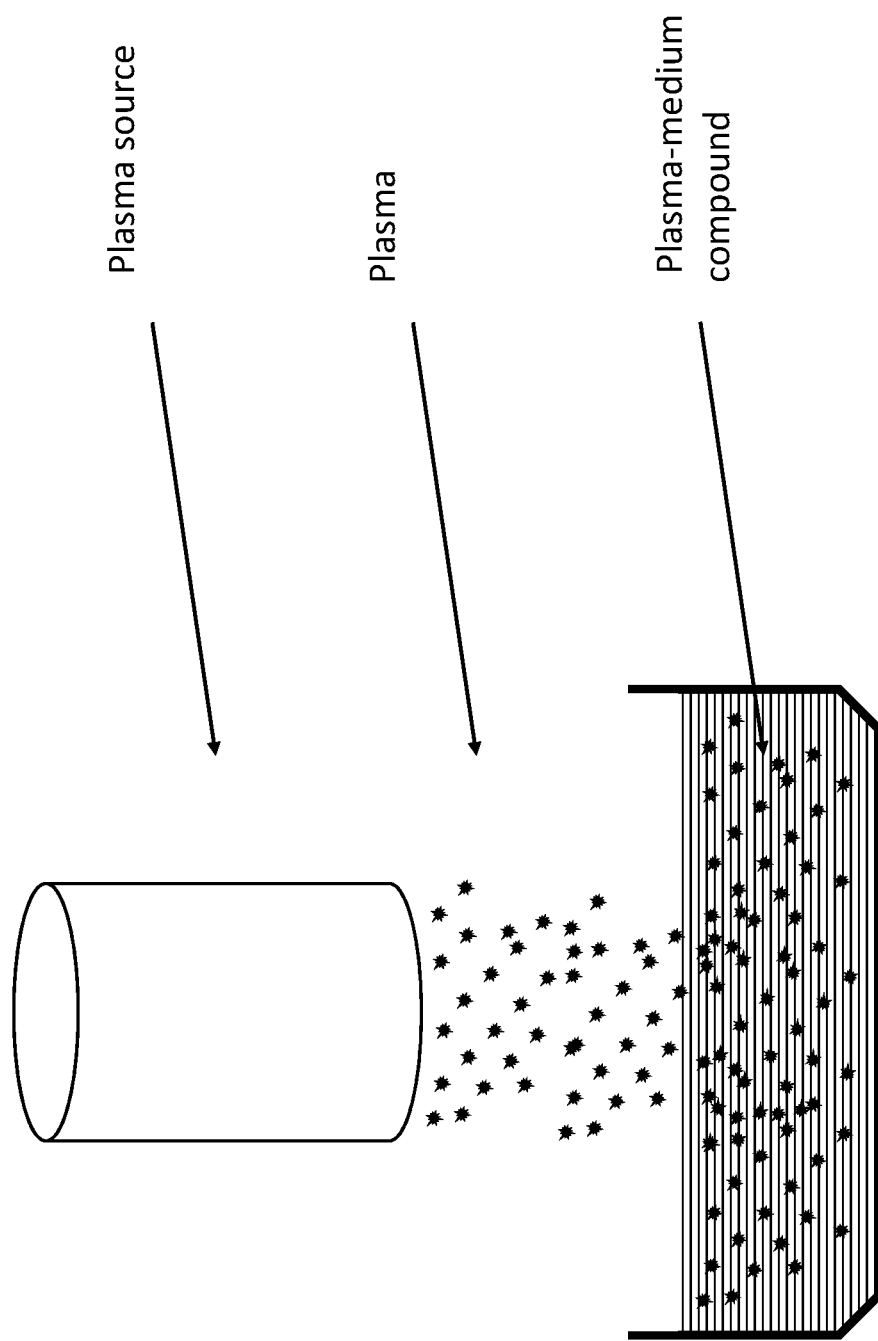
FIG. 5C is a diagrammatic elevation view of the setup of FIG. 5 taken at a time after that of FIG. 5B, wherein much of the generated plasma has been incorporated into the plasma, forming an NAP-medium compound of the present invention
Figure 5D:
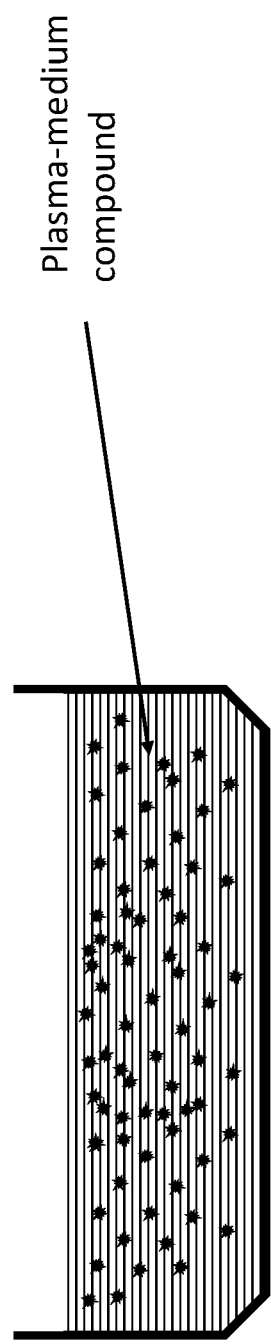
FIG. 5D is a diagrammatic elevation view of the container of FIG. 5C taken at a time after that of FIG. 5C, showing an NAP-medium compound of the present invention in a container.
Figure 6A:
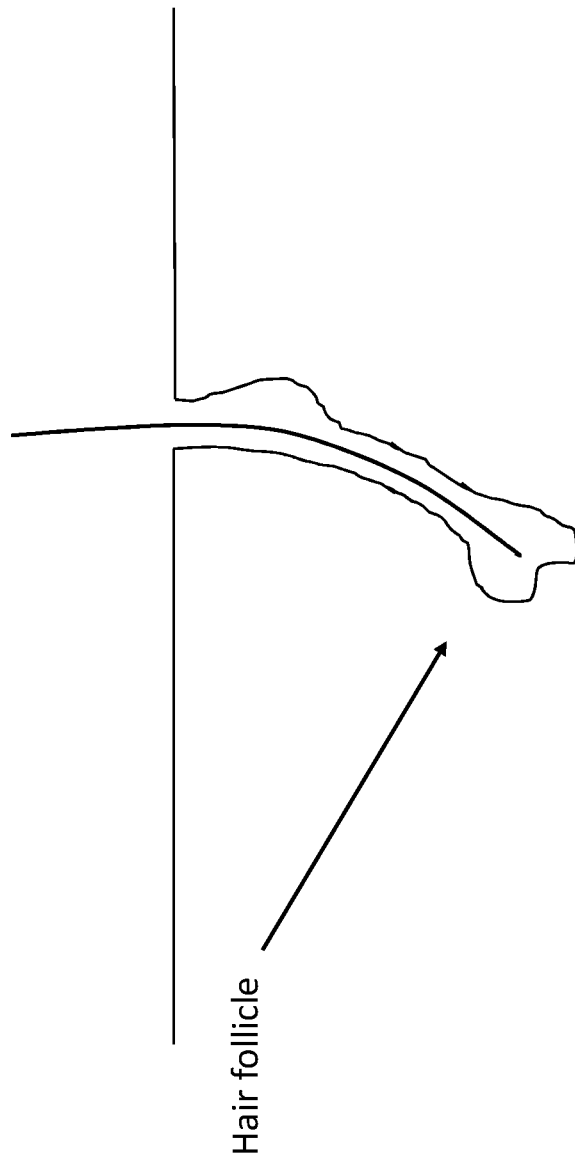
FIG. 6A is a diagrammatic magnified view of a cross-section of a subject's scalp, showing a hair follicle before being treated via a third method of the present invention.
Figure 6C:
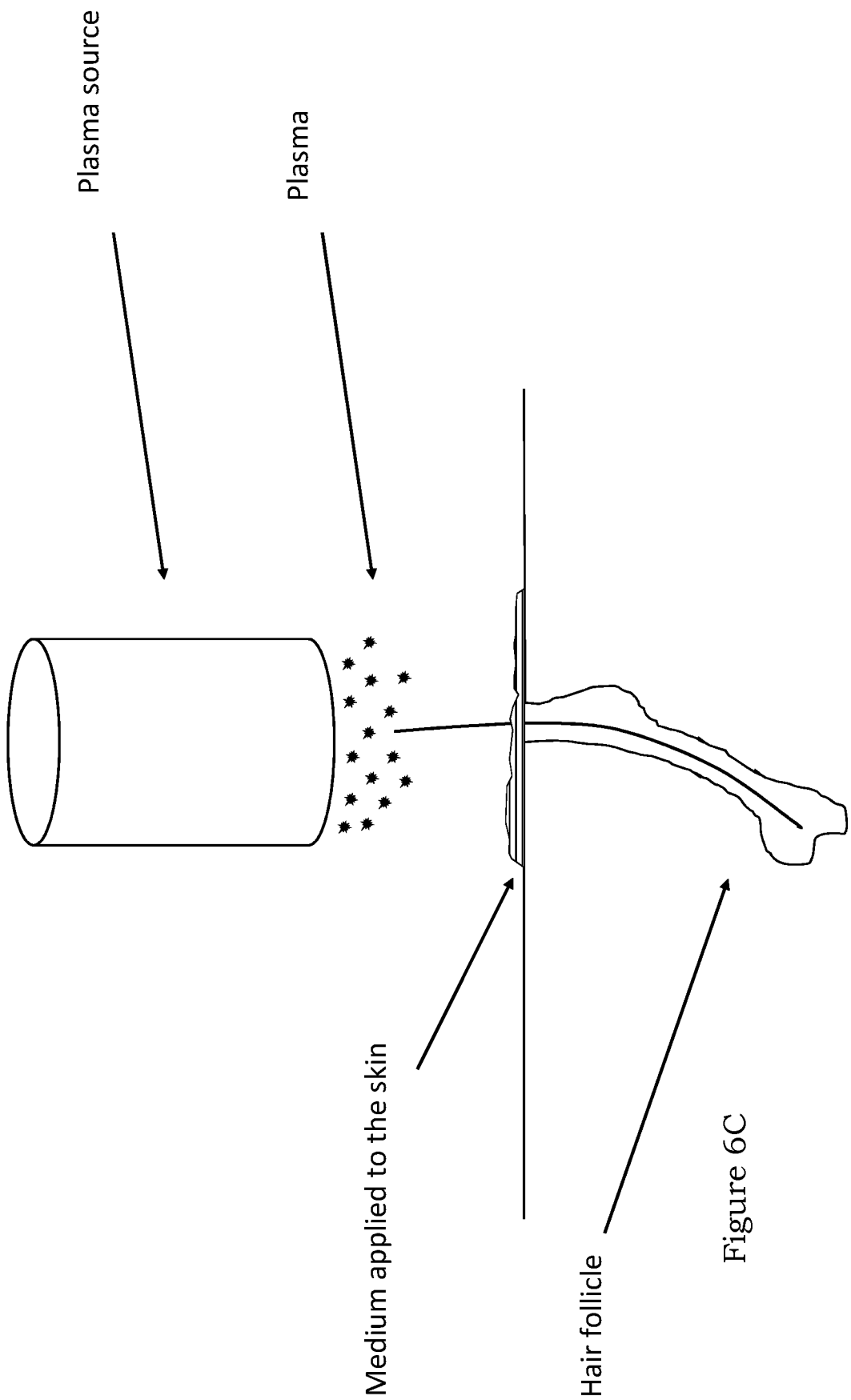
FIG. 6C is a diagrammatic magnified view of the cross-section of FIG. 6B showing a source of plasma (NAP) generating plasma after the medium has been applied as shown in FIG. 6B.
Figure 6D:
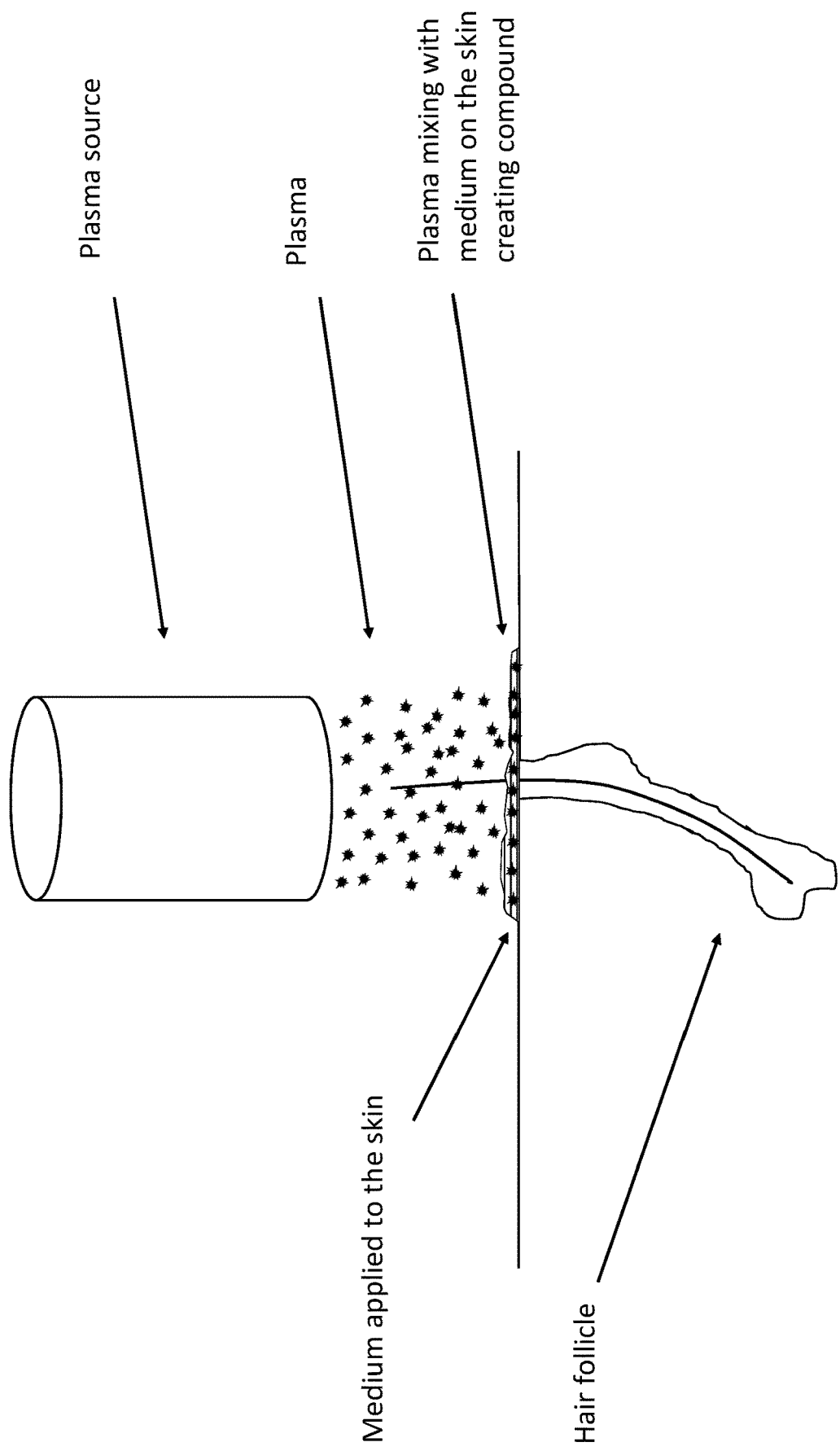
FIG. 6D is a diagrammatic magnified view of the cross-section of FIG. 6C taken at a time after that of FIG. 6C, showing plasma (NAP) mixing with the medium on the subject's skin, creating a NAP-medium compound on the skin surface immediately above the hair follicle.
Figure 6E:
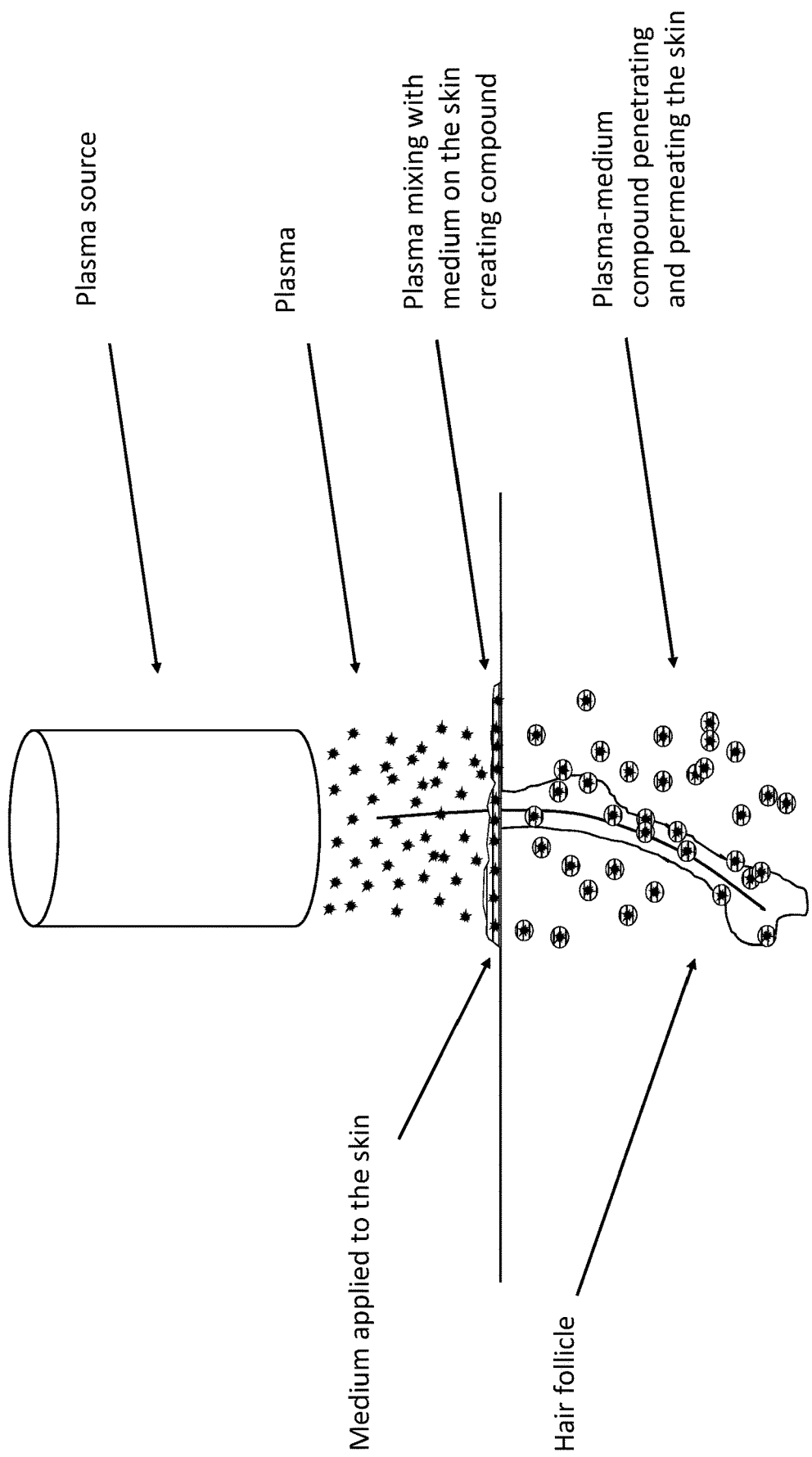
FIG. 6E is a diagrammatic magnified view of the cross-section of FIG. 6D taken at a time after that of FIG. 6D, showing plasma (NAP) mixing with the medium on the subject's skin, creating a NAP-medium compound on the skin surface immediately above the hair follicle, wherein the plasma-medium compound is penetrating and permeating the skin down to the hair follicle.

The medium is treated with a plasma source as aforesaid, and then the resulting NAP-medium compound is placed into syringes. As shown in FIG. 5E, a small quantity (0.1-0.5 cc) of NAP-medium compound is injected in multiple injections throughout the entire treated area using a small-bore hypodermic needle to reach the depth of the hair follicle.

For intralesional injection, the NAP treatment may be used as an add-on enhancer of conventional intralesional treatments for hair loss. That is, PRP, or any other medication, such as Kenalog®, that can be treated with a plasma source before being injected into the skin.

An alternative mode of delivery is via a pneumatic injection device that is a needle-less injection system, such as the DermoJet™ or MadaJet™. See: Current trends in needle-free jet injection: an update. Clin. Cosmet. Investig. Dermatol. 2018; 11: 231-238. doi: 10.2147/CCID.S162724

The NAP-medium compound may also be applied to the skin surface after pretreatment with the technique called microneedling that also enhances deep penetration of topically-applied substances. For topical applications, a non-fluid medium is preferred, but alternatively a liquid may be used. For example, the NAP-medium compound can be formulated as a lipophilic cream, hydrophilic cream ointment, lotion, or gel to enhance absorption and increase ease of application. Alternatively, the lipophilic cream, hydrophilic cream, ointment, lotion or gel may serve as the medium and be treated with a plasma source directly and the resulting NAP-medium compound in its respective form used as a treatment, immediately.

Alternatively, a medium may be applied to an affected area of the scalp. The medium is then treated in place with a plasma source to generate the NAP-medium compound in situ for direct treatment. It is preferred that the medium for such applications be a lipophilic cream, a hydrophilic cream, an ointment, a lotion, or a gel vehicle, but alternatively a liquid may be used.

EXAMPLES

Example 1

To generate plasma, one may use a pulse generator supplying microsecond pulsed electric current, connected to a 2 cm diameter copper electrode covered with a 1 mm thick quartz dielectric layer. As another example, one may provide 20-kV pulse of 20-ns pulse width at 200 Hz applied to a 5-mm diameter quartz-covered copper electrode of 10-cm length and 1-mm quartz thickness. These nanosecond pulse parameters are to be chosen to provide sufficient treatment dose at the high level of plasma uniformity required to deliver sufficient amounts of plasma while avoiding any damage to the target.

Example 2

An aqueous alcohol medium (in liquid, cream, or hydrogel form) is applied to the designated treatment area. Following such application, cold plasma (NAP) treatment is performed directly on the skin surface where the media was applied. The mixing of the media and the NAP takes place at the treatment site, providing immediate delivery of plasma components to the target. The treatments are repeated at set intervals between once a day to once a month. This procedure is schematically illustrated in FIGS. 6A to 6E.

Example 3

Five cc of normal saline solution is treated with a helium plasma jet device for 40 minutes. The plasma-medium compound is mixed with 30 grams of Vanicream™ Cream base. The patient is instructed to apply a fingertip amount of the product to the treated area, creating a thin, even film twice a day. This procedure is schematically illustrated in FIGS. 4A to 4E.

Example 4

Normal saline (4.2 cc) is treated with a DBD plasma device for 30 minutes, producing a NAP-medium compound. The NAP-medium compound is then mixed with 9.8 cc ethanol. The patient is instructed to apply 1 cc of the product to the treatment area twice a day.

Example 5

The patient is seated. The treatment area is a divided into 5×5 cm sections. The borders of the sections are marked with a skin marker. Medisca® Hydrogel, a clear, non-scented silicone-in-water microemulsion, is applied in a thin layer to a previously marked 5×5 cm section of the area. A helium jet plasma device is used to deliver plasma to the section by slowly and continuously moving the plasma stream repeatedly over the entire section for 20 minutes. The procedure is repeated until all sections of the treatment area receive treatment. This procedure is schematically illustrated in FIGS. 6A to 6E.

Example 6

The patient is seated. The treatment area is a divided into 2×2 cm sections. The borders of the sections are marked with a skin marker. Vanicream™ Moisturizing Ointment in a thin layer is applied to a previously marked 2×2 cm section of the treated area. A DBD plasma device is used to deliver plasma to the section by placing the dielectric-covered electrode a 1 mm distance from the skin with the applied Vanicream ointment. The electrode is kept in place for 10 minutes. The procedure is repeated until all sections of the treatment area receive treatment. This procedure is schematically illustrated in FIGS. 6A to 6E.

Example 7

Twenty cc Sodium Chloride Bacteriostatic Injection Solution 0.9% is treated with a helium jet plasma for 50 minutes under sterile conditions. The NAP-medium compound is transferred under sterile conditions to two 10-cc Luer lock syringes, which are then connected to 25-gauge hypodermic needles. The treated area is prepped: the area is thoroughly wiped with Hibiclens® disinfectant. The area is then treated with subdermally injected 0.3 cc amounts of the plasma-medium compound. The injection sites are placed evenly. This procedure is schematically illustrated in FIGS. 5A to 5E.

Example 8—Clinical Trial

The goal of this short pilot study was to assess the tolerability and practicality of the plasma-medium compound treatment, to pave the way for longer studies assessing efficacy.

A review of the electronic medical record system was performed to identify patients seen during the preceding 12 months with the diagnosis of alopecia. Each patient was contacted and was offered participation in a screening for hair loss treatment clinical trial. Inclusion criteria were: active hair loss, ability to keep appointments for regular evaluation. Exclusion criteria were active scalp disease, use of any type of hair growth treatment in the past 3 months. After screening 13 patients (8 female and 5 male) were enrolled in the study after an informed consent process. The study consisted of twice daily application of 1 ml plasma-medium compound to the scalp for four months. The solution was given to the patients in 14 ml amounts once a week in bottles equipped with droplet applicators. The patients were instructed in the application of the compound. The patients were seen weekly for visual scalp inspection to ensure the early detection of any adverse effects. At the end of the trial the participants answered questions regarding the treatment.

Eleven (11) patients completed the trial, two (females) dropped out due to inability to keep the weekly appointments. 5 males and 6 females completed the trial.

Results:
- 10 out of 11 patients found the application procedure practical.
- 11 out of 11 patients found the application procedure easy to perform.
- 1 out of 11 patients reported side effects: transient burning sensation of the scalp, which resolved without treatment after suspending treatment for several days and did not recur after restarting treatment
- 9 out of 11 patients noticed positive effects from the treatment. The effects varied patient-to-patient and included less shedding, increased growth of existing hair, growth of 'baby hair'.

Although I have described the present invention by giving various examples in the description above, it is to be understood that the scope of the exclusive rights granted by the patent is defined by each of the claims.

In the following claims, the phrase "consisting essentially of" or "consists essentially of" limits the scope of the recited item(s) to the specified materials or steps and those that do not materially affect the basic and novel characteristic(s) of the claimed invention. The term "NAP-medium compound" refers to the substance that results from the mixing of NAP and the recited medium. The term should not be interpreted as specifying that the substance is a chemical compound having molecules composed of covalently bonded atoms, or even that a NAP-medium compound must be homogeneous.

The invention claimed is:

1. A method of ameliorating hair loss comprising the step of applying a Non-thermal Atmospheric Plasma medium compound (NAP-medium compound) to an affected area at least once a day for at least a month, wherein said NAP-medium compound comprises,
   a. a medium selected from the group consisting of water, other aqueous media, and water-soluble media, and
   b. non-thermal atmospheric plasma (NAP) generated from a plasma source, and
   c. allowing the NAP-medium compound to permeate the hair follicle area.

2. The method of ameliorating hair loss of claim 1, wherein the NAP-medium compound is formulated as a lipophilic cream, a hydrophilic cream, an ointment, a lotion, or a gel vehicle.

3. A method of ameliorating hair loss from an affected area of the scalp comprising the following steps:

a. generating a suitable NAP-medium compound from a suitable pharmaceutically-acceptable medium;
b. introducing the NAP-medium compound into a syringe-type device;
c. injecting the NAP-medium compound into the scalp subcutaneously;
d. allowing the NAP-medium compound to permeate the hair follicle area to induce growth;
   wherein the pharmaceutically acceptable medium is selected from the group of ethanol, glycerin, isopropyl alcohol, methanol, propylene glycol, water, saline, phosphate buffered saline, culture medium, Ringer's lactate solution, PRP blood plasma, and mixtures thereof.

4. A method of ameliorating hair loss from an affected area of the scalp comprising the following steps:
a. applying a pharmaceutically-acceptable medium to the affected area of the scalp,
b. treating the medium present on the scalp with NAP from a plasma source; and
c. allowing the resulting in situ-generated NAP-medium compound to remain on the affected area of the scalp, whereby it penetrates the scalp sufficiently to provide the hair-growth inducing effect of NAP;
   wherein, the medium consists essentially of one or more of water, saline, phosphate buffered saline, culture media, Ringer's lactate solution, platelet rich blood plasma (PRP), methanol, ethanol, isopropanol, propylene glycol, glycerol, lanolin alcohols and mixtures thereof.

5. The method of claim 4, wherein the pharmaceutically-acceptable medium is formulated as a lipophilic cream, a hydrophilic cream, an ointment, a lotion, or a gel vehicle.

* * * * *